(12) United States Patent
Hassan et al.

(10) Patent No.: US 8,685,445 B2
(45) Date of Patent: Apr. 1, 2014

(54) ENTERIC COMPOSITION FOR THE MANUFACTURE OF SOFT CAPSULE WALL

(75) Inventors: Emadeldin M. Hassan, Greensboro, NC (US); Aqeel A. Fatmi, Greensboro, NC (US); Nachiappan Chidambaram, High Point, NC (US)

(73) Assignee: Banner Pharmacaps Inc., High Point, NC (US)

( * ) Notice: Subject to any disclaimer, the term of this patent is extended or adjusted under 35 U.S.C. 154(b) by 2697 days.

(21) Appl. No.: 10/529,984

(22) PCT Filed: Jun. 27, 2003

(86) PCT No.: PCT/US03/20579
§ 371 (c)(1),
(2), (4) Date: Mar. 31, 2005

(87) PCT Pub. No.: WO2004/030658
PCT Pub. Date: Apr. 15, 2004

(65) Prior Publication Data
US 2006/0165778 A1    Jul. 27, 2006

Related U.S. Application Data

(60) Provisional application No. 60/415,187, filed on Oct. 1, 2002.

(51) Int. Cl.
*A61K 9/56*    (2006.01)

(52) U.S. Cl.
USPC ............................................................ 424/456

(58) Field of Classification Search
USPC ................................................. 424/451, 456
See application file for complete search history.

(56) References Cited

U.S. PATENT DOCUMENTS

| | | | | |
|---|---|---|---|---|
| 3,826,666 | A | * | 7/1974 | Hirai et al. ................. 106/139.3 |
| 4,138,013 | A | * | 2/1979 | Okajima ....................... 206/528 |
| 4,500,453 | A | * | 2/1985 | Shank ........................... 530/354 |
| 4,790,881 | A | | 12/1988 | Wittwer et al. |
| 4,816,259 | A | * | 3/1989 | Matthews et al. ............. 424/463 |
| 5,194,464 | A | * | 3/1993 | Itoh et al. ......................... 524/42 |
| 6,331,316 | B1 | * | 12/2001 | Ullah et al. ................... 424/482 |
| 2001/0051188 | A1 | * | 12/2001 | Ullah et al. ................... 424/493 |

FOREIGN PATENT DOCUMENTS

| | | |
|---|---|---|
| DE | 3222476 | 12/1983 |
| EP | 0092908 | 11/1983 |
| EP | 1 184 033 | 3/2002 |
| WO | WO 98/50019 | 11/1998 |
| WO | WO 00/67723 | 11/2000 |
| WO | WO 01/24780 | 4/2001 |

\* cited by examiner

*Primary Examiner* — Samantha Shterengarts
(74) *Attorney, Agent, or Firm* — Womble Carlyle Sandridge & Rice, LLP

(57) ABSTRACT

A gel mass is provided that is useful in manufacturing enteric soft or hard capsules, or enteric tablets without coating.

18 Claims, No Drawings

ENTERIC COMPOSITION FOR THE MANUFACTURE OF SOFT CAPSULE WALL

The present application is a National Phase Application under §371 of International Application Serial Number PCT/US03/20579, filed on Jun. 27, 2003, which claims benefit of priority to U.S. Provisional Application Ser. No. 60/415,187, filed on Oct. 1, 2002.

FIELD OF THE INVENTION

The present invention relates to enteric preparations, More particularly, the invention relates to enteric solid dosage forms made using a gel mass comprising a film-forming, water-soluble polymer, an acid-insoluble polymer, and, optionally, other ingredients such as plasticizers, colors, and flavors. The invention further provides a direct method for manufacturing enteric preparations without need for coating.

BACKGROUND OF THE INVENTION

The use and manufacture of enteric dosage forms are well known to skilled personnel. Such dosage forms have been explained and reviewed in reference works, e.g., in Remington's Pharmaceutical Sciences, 18$^{th}$ edition, Mack Publishing Co., Easton, Pa. (1990). Enteric dosage forms are desirable, either to protect the content of the dosage form from the gastric conditions or to protect the gastric tissue from an irritant material contained in the enteric dosage form. A further use for enteric dosages is prevention of a lasting, unacceptable mouth odor resulting from ingestion of substances like garlic or fish oil. Enteric dosage forms are also used to provide slow or delayed release of a substance.

To fulfill the compendium definition requirement for enteric or gastro-resistant preparations, these preparations have to pass specific compendia tests. The enteric or gastro-resistant property is obtained only if the enteric dosage form does not dissolve or disintegrate in gastric acidity for a specified amount of time (usually two hours in 0.1 N hydrochloric acid at 37° C.). Further, the enteric dosage forms must release their contents in simulated intestinal environments (e.g., in buffers of pH values at about 6.8 within certain time periods). Detailed evaluation techniques are described in national and international pharmacopoeia such as United States Pharmacopoeia.

The majority, if not all, of the enteric dosage forms currently in use are produced by a film-coating process, where a thin film layer of acid-insoluble (enteric) polymer is accumulated on the surface of an pre-manufactured dosage form. Dosage forms coated in this manner have been mainly tablets and, to a lesser extent, hard or soft capsules. The enteric coating method involves spraying of an aqueous or organic solution or a suspension of enteric polymers onto tumbling or moving tablets or capsules, accompanied by drying using hot air.

Enteric dosage forms made by coating suffer from various process-related problems and defects that affect their performance or appearance. For example, "orange peel" surface formation, also known as surface roughness, mottling, or lack of surface homogeneity may result. And more seriously, coat integrity failure may occur, such as in cases of cracking or flaking off of the coating. All coatings present inherent problems, including possible uneven distribution of the coating ingredients, which can easily happen under the multivariate coating process.

The foregoing problems of enteric coatings are shared by all enteric dosage forms such as tablets and capsules. However, the problems faced during coating of capsules are even more critical, due to the delicate and heat sensitive nature of the soft elastic capsule shell. Both hard and soft capsules can easily undergo agglomeration and distortion due to the heat-sensitive shell composition. Moreover, the smoothness and elasticity of the capsule surface make it difficult to form an intact adhering enteric coat without careful sub-coating step to improve the surface for coating. A further disadvantage of enteric coating for soft capsules is the loss of the normally shiny and clear appearance of capsule gelatin shells. The elegant, clear gelatin shell has been a significant reason for soft capsule popularity and acceptance. In addition to the undesirable surface texture modifications usually caused by coating, most accepted aqueous enteric polymer preparations result in opaque capsules.

While different attempts have been tried to improve the manufacture of enteric soft gelatin capsules via coating, the inherent disadvantages in the coating process amplify the necessity for a better way of manufacturing enteric soft capsules, ideally, without coating. Enteric coatings (both sub-coating and over-coatings) and enteric polymers are discussed or suggested generally in U.S. Pat. Nos. 4,518,433, 4,816,259, and 5,330,759. None of these references, however, teach or suggest the invention as set forth herein.

SUMMARY OF THE INVENTION

One aspect of this invention is a gel mass composition that can be used to manufacture enteric oral dosage forms such as tablets or capsules, without the need of coating. A second aspect of this invention is a filled enteric soft capsule that does not require enteric coating or cross-linking to gain its enteric character. According to this aspect of the invention, fill materials can be hydrophilic or hydrophobic in nature. Fill materials can also be liquid, solid or a combination thereof. A third aspect of this invention is a soft capsule enteric shell composition that contains a film-forming polymer, an acid-insoluble polymer, and, optionally, plasticizers, colors, and/or other conventionally accepted pharmaceutical additives. The gel mass composition of the invention avoids significant loss of physical strength or viscosity of the film-forming polymer.

A fourth aspect of this invention is a process of preparing a gel mass from which the enteric capsule shell is made. According to the process of this aspect of the invention, an alkali is used at a level allowing dissolution of the acid-insoluble polymer without negatively affecting the film-forming polymer integrity, its physical strength, or its viscosity. A fifth aspect of this invention is a process of manufacturing filled enteric soft capsules using cast gel mass and a rotary die encapsulation machine, such as that disclosed in U.S. Pat. Nos. 5,146,730 and 5,459,983, incorporated herein by reference and commonly owned by the assignee of this application. A sixth aspect of this invention is production of clear enteric soft capsules. A seventh aspect of this invention is the production of transparent, yet colored, enteric soft capsules. An eighth aspect of the invention is the use of the foregoing aspects for delivering food and medicine.

The gel mass compositions of this invention are further useful to manufacture enteric solid oral dosage forms such as tablets, and hard and soft capsules without the conventional coating technique. A preferred method of manufacturing enteric tablets with this invention is to use enrobement techniques and a rotary die as described in U.S. Pat. Nos. 6,482,516 and 5,459,983, and 5,146,730, all fully incorporated herein by reference. Gel compositions of this invention are also useful to make clear or opaque hard capsules using regular equipment known in the art.

Accordingly, the present invention relates to a gel mass composition comprising a film-forming, water-soluble polymer, an acid-insoluble polymer, and, optionally, at least one plasticizer, an optional coloring agent and an aqueous solvent. The gel mass is useful in manufacturing enteric soft or hard capsules, or enteric tablets without coating.

The film-forming, water-soluble polymer can be of proteinaceous nature, such as gelatin. In one embodiment, the gelatin is extracted from animal bones or skins, and has about 100 to about 250 blooms.

In another embodiment, the film-forming, water-soluble polymer can be of carbohydrate nature such as hydroxypropyl methylcellulose or methyl cellulose. The acid-insoluble polymer can also be selected from the group consisting of acrylic and methacrylic acid copolymers, cellulose acetate esters such as phthalate, butyrate, hydroxypropyl methyl cellulose phthalate, and salts thereof.

The shell composition of the invention can contain at least one plasticizer selected from the from the group consisting of sorbitol, glycerol, polyethylene glycol, poly-alcohols with 3 to 6 carbon atoms, citric acid, citric acid esters such as triethyl citrate, and combinations thereof.

The solvent used can be water or aqueous solution of alkalis, such as ammonia, sodium hydroxide, potassium hydroxide, ethylene diamine, hydroxylamine, tri-ethanol amine, or hydroalcoholic solutions of the same. The alkali can adjusted such that the final pH of the gel mass is less than or equal to about 9.0 pH units. In another embodiment, the alkali is adjusted such that the pH does not exceed 8.5. In yet another embodiment, the alkali is adjusted such that the pH does not exceed 8.0. The alkali can be a volatile alkali such as ammonia or ethylene-diamine.

Generally, it is noted that the compositions of the invention are characterized by a consistency compatible with desirable process handling, such as rotary die processing for capsule formation. Without wishing to be bound by a particular theory, it appears that the compositions of the invention avoid undue degradation of the film-forming, water-soluble polymer by avoiding excessively alkaline conditions during processing.

The invention also relates to a process of manufacturing a shell composition into soft capsules. The process includes preparing a solution comprising a film-forming, water-soluble polymer and an acid-insoluble polymer and mixing with appropriate plasticizers to form a gel mass; casting gel mass into films or ribbons using heat-controlled drums or surfaces; and manufacturing a soft capsule using rotary die technology. The thickness of the films or ribbons is from about 0.015 inches to about 0.050 inches. In one embodiment, the thickness is about 0.020 inches.

The moisture content of the shell composition can be from about 2% to about 10%. The moisture content can also be from about 4% to about 8%. The moisture content of particular embodiments is about 8%.

The invention also relates to an enteric gel composition having an enteric polymer to film-former polymer ratio of from about 20:80 to about 45:55.

The invention also relates to an enteric gel composition having a plasticizer to polymer ratio from about 10% to about 50% of the polymer weight. In one embodiment, the ratio is about 25%.

Capsules prepared in accordance with the methods of the invention can be used to contain a hydrophilic fill solution or suspension containing polyethylene glycol. Alternatively, the fill composition can be a hydrophobic solution or suspension, such as vegetable oils or shortening, or waxes, or combinations thereof.

The present invention provides enteric, gel mass compositions that do not require cross-linking to achieve the desired enteric properties. Cross-linking treatments can cause potential toxicity concerns, and can lead to an uncontrolled process which lead to a product subject to deterioration over time. Further, such cross-linking adds an additional step to the manufacturing process.

DETAILED DESCRIPTION OF THE INVENTION

This invention discloses a composition, process of manufacture and use of enteric oral solid dosage forms, namely tablets, and hard and soft capsules that do not require a coating or cross-linking in order to possess enteric properties. The gel mass of this invention can be made by mixing a film-forming polymer with an acid-insoluble polymer, and plasticizing materials to form a homogeneous mixture, in presence of a solvent.

In a one embodiment, the invention provides an acid-insoluble polymer within the film-former mass that renders the total mass an enteric material, at relatively low concentrations of the acid-insoluble polymer (from about 8% to about 20% of the total wet gel mass) and without the need of excessive amounts of alkali, thus avoiding degradation or weakening of the film-forming polymer. In one embodiment, the ratio of acid-insoluble polymer to film-forming polymer is greater than about 1:4.

Films made by casting the final gel mass do not dissolve or disintegrate in acids, such as 0.1 M hydrochloric acid, despite the fact that the majority of shell ingredients (more than 50%) normally dissolve in, or are miscible with, acids. Enteric films made using the disclosed compositions remain substantially intact in hydrochloric acid. Further, enteric films of this invention reduce migration of small molecules such as methylene blue through them in acidic environments. In another embodiment, the final gel mass provides films of increased strength without substantially compromising film elasticity. Moreover, casting films according to the invention are able to be sealed at normal temperature range typically used for making softgel capsules (from about 80° F. to about 105° F.) or can be used to surround or enrobe tablets to make them enteric. The gel masses can also be cast around pins to form two-piece hard capsules as illustrated in Remington's Pharmaceutical Sciences, $18^{th}$ edition, published by Mack Publishing Co., Easton, Pa. (1990)

Examples of film-former polymers that are useful in this invention can be of natural origin, preferably gelatin, or of synthetic nature such as hydroxypropyl methyl cellulose. Examples of acid-insoluble polymers are cellulose acetate phthalate (CAP), cellulose acetate butyrate, hydroxypropyl methyl cellulose phthalate, algenic acid salts such as sodium or potassium alginate, shellac, acrylic acid-methacrylic acid copolymers (available under the trade name of EUDRAGIT (Rohm America Inc., Piscataway, N.J.) as powder or 30% aqueous dispersion, or under the trade name of EASTACRYL as 30% dispersion (Eastman Chemical Company, Kingsport, Tenn.), and sodium alginate. Acrylic-methacrylic acid copolymers are particularly stable and may be preferred in some embodiments. Acid-insoluble polymers specifications are detailed in the United States Pharmacopoeia.

Useful plasticizers according to the invention are glycerol, sorbitol, polyethylene glycol, citric acid, citric acid esters, such as tri-ethyl citrate, or combinations thereof. The composition ratio between the film-former and the acid-insoluble polymer is adjusted so that the gel mass can be made into soft capsules. Without being limited to any mechanism of performance, it has been discovered that enteric capsules can be made with an acid-insoluble polymer comprising as little as about 8% of the total content of the wet shell mass, and as high as about 30% of the total wet shell mass. The weight ratio range of acid-insoluble polymer/film-former polymer is from about 25% to about 50%. The range can be from about 30% to about 40%.

In one embodiment of the process aspect of the invention, enteric gel masses can be made by dissolving the acid-insoluble polymer powder in aqueous solution of an alkali such as ammonia, sodium hydroxide, or potassium hydroxide, or liquid amines such as tri-ethanol amine or ethylene diamine. The amount of alkali is adjusted to give a final pH value of the gel mass less than or equal to about 9.0 pH units. In one embodiment, the final pH does not exceed 8.5. Volatile alkalis such as ammonia and ethylene diamine are preferred. The film-former can then be wetted by the plasticizer and mixed with the acid-insoluble gel to make a final homogeneous mix in a heat-controlled vessel and can be degassed by using vacuum. The alkali concentrations do not require an additional step such as heating or neutralizing with acid in order to neutralize the gel mass or the finished capsules.

In another embodiment of the process aspect of the invention, the enteric gel can be made by using a ready-made aqueous dispersion of the acid-insoluble polymer by adding alkaline materials such as ammonium, sodium, or potassium hydroxides or other alkalis that will cause the acid-insoluble polymer to dissolve, such as triethanol amine or ethylene diamine or a combination thereof. The plasticizer-wetted, film-forming polymer can then be mixed with the solution of the acid-insoluble polymer. In a third embodiment of the process aspect of this invention, acid-insoluble polymers in the form of salts of the above-mentioned bases or alkalis can be dissolved directly in water and mixed with the plasticizer-wetted, film-forming polymer.

The enteric composition of the invention, comprising a film-forming polymer (e.g., gelatin or a synthetic polymer) and at least one enteric, acid-insoluble polymer, can be used to contain a fill that is liquid, semi-solid, or solid.

EXAMPLES

Example 1

Enteric Gel Mass

A gel mass was made according to the formula below. The acid-insoluble polymer, EUDRAGIT L 100 was dissolved in the water-alkali vehicle, and triethyl citrate was then added. The film-forming polymer, gelatin (lime bone, 150 bloom) was mixed with the plasticizer, glycerol, and added to the enteric polymer solution, mixed for 2 hours and kept overnight at 60° C.

| | |
|---|---|
| Gelatin | 36.00% |
| EUDRAGIT L 100 | 9.00% |
| Glycerol | 18.00% |
| Triethyl citrate | 0.90% |
| Ammonium Hydroxide (30% w/v) | 2.40% |
| Water | 33.70% |

Example 2

Enteric Soft Capsules with Oil-Based Fill

Gel mass of Example 1 was cast as a ribbon with 0.03" thickness on a cold drum (10° C. to 13° C.). This ribbon was utilized for encapsulation of medium chain tryiglyceride oil using 7.5 oval die. The capsules were dried and subjected for dissolution/disintegration testing as per the requirement of current USP.

Example 3

Enteric Soft Capsules with Oil-Based Fill

Gel mass of Example 1 was cast into a ribbon with 0.03" thickness on a cold drum (10° C. to 13° C.). This ribbon is utilized for encapsulation of medium chain tryiglyceride oil using 12 oval die. The capsules were dried and subjected for dissolution/disintegration analysis as per the requirements of current USP.

Example 4

Enteric Soft Capsules with Oil-Based Fill

Gel mass of Example 1 was casted as a ribbon with 0.03" thickness on a cold drum (10° C. to 13° C.). This ribbon is utilized for encapsulation of medium chain tryiglyceride oil using 20 oblong die. The capsules were dried and subjected for dissolution/disintegration analysis as per the requirements of current USP.

Example 5

Enteric Soft Capsules with Oil-Based Fill Containing a Biphosphonate

| | |
|---|---|
| Alendronate Sodium | 1.54% |
| Hydrogenated Soybean Oil | 7.45% |
| Soybean Oil | 83.55% |

Hydrogenated soybean oil was melted at 65° C. with soybean oil and to this mixture, Alendronate sodium was added and mixed using homogenizer at 1000 rpm for 5 minutes.

Gel mass of Example 1 was cast as a ribbon with 0.03" thickness on a cold drum (10° C. to 13° C.). This ribbon is utilized for encapsulation of above mentioned fill using 7.5 oval die. The capsules were dried and subjected to dissolution/disintegration analysis as per the requirements of current USP.

Example 6

Enteric Soft Capsules with Hydrophilic Fill

| | |
|---|---|
| Alendronate Sodium | 1.26% |
| Polyethylene glycol (3350) | 4.94% |
| Polyethylene glycol (400) | 93.80% |

Polyethylene glycol was melted at 55° C. with polyethylene glycol (400) and to this mixture, Alendronate sodium was added and mixed using a homogenizer at 1000 rpm for 5 minutes.

Gel mass of Example 1 was cast into a ribbon with 0.03" thickness on a cold drum (10° C. to 13° C.). This ribbon is utilized for encapsulation of above mentioned fill using 7.5 oval die. Capsules were dried and subjected to dissolution/disintegration analysis as per the requirements of current USP.

Example 7

Enteric Soft Capsules with a Hydrophilic/Hydrophobic Fill

| | |
|---|---|
| Alendronate Sodium | 1.26% |
| Water | 10.00% |
| Hydrogenated Soybean Oil | 7.47% |
| Vegetable Shortening | 7.47% |
| Soybean Oil | 73.50% |

Alendronate sodium was dissolved in water (part 1). Hydrogenated soybean oil and vegetable shortening was melted at 65° C. with soybean oil (art 2). Part 1 and 2 is mixed and passed five times through the MICROFLUIDIZER® at 10,000 psi.

Gel mass of example 1 was casted as a ribbon with 0.03" thickness on a cold drum (10° C. to 13° C.). This ribbon was utilized for encapsulation of above mentioned Alendronate fill using 7.5 oval die. The capsules were dried and subjected for dissolution/disintegration analysis as per the requirements of current USP.

Example 8

Enteric Gel Mass

A gel mass was made according to the formula below. The acid-insoluble polymer, EUDRAGIT L 100 was dissolved in the water-alkali vehicle, triethyl citrate was then added. The film-forming polymer, gelatin (lime bone, 150 bloom) was mixed with the plasticizer, glycerol. And added to the enteric polymer solution, mixed for 2 hours and was kept overnight at 60° C.

| | |
|---|---|
| Gelatin | 36.00% |
| EUDRAGIT L 100 | 9.00% |
| Glycerol | 18.00% |
| Triethyl citrate | 0.90% |
| Sodium Hydroxide | 2.80% |
| Water | 33.30% |

Example 9

Enteric Soft Capsules with Oil-Based Fill

Gel mass of Example 6 was cast into a ribbon with 0.03" thickness on a cold drum (10° C. to 13° C.). This ribbon was utilized for encapsulation of medium chain tryiglyceride oil using 12 oval die. The capsules were dried and subjected for dissolution/disintegration analysis as per the requirement of current USP.

Example 10

Enteric Soft Capsules with Oil-Based Fill

Gel mass of example 6 was cast into a ribbon with 0.025" thickness on a cold drum (10° C. to 13° C.). This ribbon was utilized for encapsulation of medium chain tryiglyceride oil using 12 oval die. The capsules were dried and subjected for dissolution/disintegration analysis as per the requirement of current USP.

Example 11

Enteric Soft Capsules with Oil-Based Fill

Gel mass of example 6 was cast into a ribbon with 0.020" thickness on a cold drum (10° C. to 13° C.). This ribbon was utilized for encapsulation of medium chain tryiglyceride oil using 12 oval die. The capsules were dried and subjected for dissolution/disintegration analysis as per the requirement of current USP.

Example 12

Enteric Soft Capsules with Oil-Based Fill

Gel mass of example 6 was cast into a ribbon with 0.015" thickness on a cold drum (10° C. to 13° C.). This ribbon was utilized for encapsulation of medium chain tryiglyceride oil using 12 oval die. The capsules were dried and subjected for dissolution/disintegration analysis as per the requirement of current USP.

Example 13

Enteric Gel Mass

A gel mass was made according to the formula below. The acid-insoluble polymer, EUDRAGIT L 100 was dissolved in the water-alkali vehicle, triethyl citrate was then added. The film-forming polymer, gelatin (lime bone, 150 bloom) was mixed with the plasticizer, glycerol. And added to the enteric polymer solution, mixed for 2 hours and was kept overnight at 60° C.

| | |
|---|---|
| Gelatin | 31.50% |
| EUDRAGIT L 100 | 13.50% |
| Glycerol | 17.55% |
| Triethyl citrate | 1.35% |
| Ammonium Hydroxide (30% w/v) | 3.60% |
| Water | 32.50% |

Example 14

Enteric Soft Capsules with Oil-Based Fill

Gel mass of Example 13 was cast into a ribbon with 0.050" thickness on a cold drum (10° C. to 13° C.). This ribbon was utilized for encapsulation of medium chain tryiglyceride oil using 7.5 oval die. The capsules were dried and subjected for dissolution/disintegration analysis as per the requirement of current USP.

Example 15

Enteric Soft Capsules with Oil-Based Fill

Gel mass of Example 13 was cast into a ribbon with 0.045" thickness on a cold drum (10° C. to 13° C.). This ribbon was utilized for encapsulation of medium chain tryiglyceride oil using 7.5 oval die. The capsules were dried and subjected for dissolution/disintegration analysis as per the requirement of current USP.

Example 16

Enteric Soft Capsules with Oil-Based Fill

Gel mass of example 13 was cast into a ribbon with 0.040" thickness on a cold drum (10° C. to 13° C.). This ribbon was utilized for encapsulation of medium chain tryiglyceride oil using 7.5 oval die. The capsules were dried and subjected for dissolution/disintegration analysis as per the requirement of current USP.

Example 17

Enteric Soft Capsules with Oil-Based fill

Gel mass of Example 13 was cast into a ribbon with 0.035" thickness on a cold drum (10° C. to 13° C.). This ribbon was utilized for encapsulation of medium chain tryiglyceride oil using 7.5 oval die. The capsules were dried and subjected for dissolution/disintegration analysis as per the requirement of current USP.

Example 18

Enteric Soft Capsules with Oil-Based Fill

Gel mass of Example 13 was cast into a ribbon with 0.030" thickness on a cold drum (10° C. to 13° C.). This ribbon is utilized for encapsulation of medium chain tryiglyceride oil using 7.5 oval die. The capsules were dried and subjected for dissolution/disintegration analysis as per the requirement of current USP.

Example 19

Enteric Soft Capsules with Oil-Based Fill

Gel mass of Example 13 was cast into a ribbon with 0.025" thickness on a cold drum (10° C. to 13° C.). This ribbon is utilized for encapsulation of medium chain tryiglyceride oil using 7.5 oval die. The capsules were dried and subjected for dissolution/disintegration analysis as per the requirement of current USP.

Example 20

Enteric Soft Capsules with Oil-Based Fill

Gel mass of Example 13 was cast into a ribbon with 0.020" thickness on a cold drum (10° C. to 13° C.). This ribbon is utilized for encapsulation of medium chain tryiglyceride oil using 7.5 oval die. The capsules were dried and subjected for dissolution/disintegration analysis as per the requirement of current USP.

Example 21

Enteric Soft Capsules with Oil-Based Fill

Gel mass of Example 13 was cast into a ribbon with 0.015" thickness on a cold drum (10° C. to 13° C.). This ribbon is utilized for encapsulation of medium chain tryiglyceride oil using 7.5 oval die. The capsules were dried and subjected for dissolution/disintegration analysis as per the requirement of current USP.

Example 22

Enteric Soft Capsules with Oil-Based Fill Containing Garlic

Garlic extract was mixed with soybean oil at 200 rpm using a propeller mixer.

| | |
|---|---|
| Garlic extract | 0.32% |
| Soybean Oil | 99.68% |

Gel mass of Example 13 was cast into a ribbon with 0.03" thickness on a cold drum (10° C. to 13° C.). This ribbon was utilized for encapsulation of above-mentioned garlic fill using 7.5 oval die. The capsules were dried and subjected for dissolution/disintegration analysis as per the requirements of current USP.

Example 23

Enteric Soft Capsules with Oil-Based Fill Containing Omeprazole

Vitamin E TPGS and CREMOPHOR RH40 were melted with medium chain triglyceride at 40° C. Omeprazole was added to the above mixture and mixed well.

| | |
|---|---|
| Omeprazole | 7.40% |
| Medium chain triglyceride | 63.00% |
| Vitamin E TPGS | 7.40% |
| Cremophor RH 40 | 22.20% |

Gel mass of Example 13 was casted as a ribbon with 0.03" thickness on a cold drum (10° C. to 13° C.). This ribbon is utilized for encapsulation of above mentioned Omeprazole fill using 3 oval die. The capsules were dried and subjected for dissolution/disintegration analysis as per the requirements of current USP.

Example 24

Enteric Gel Mass

A gel mass was made according to the formula below. The acid-insoluble polymer, EUDRAGIT L 100 was dissolved in the water-alkali vehicle, triethyl citrate was then added. The film-forming polymer, gelatin (lime bone, 150 bloom) was mixed with the plasticizer, glycerol. And added to the enteric polymer solution, mixed for 2 hours and was kept overnight at 60° C.

| | |
|---|---|
| Gelatin | 27.00% |
| EUDRAGIT L 100 | 18.00% |
| Glycerol | 17.10% |
| Triethyl citrate | 1.80% |
| Ammonium Hydroxide (30% w/v) | 4.80% |
| Water | 31.30% |

Example 25

Enteric Soft Capsules with Oil-Based Fill

Gel mass of Example 24 was cast into a ribbon with 0.030" thickness on a cold drum (10° C. to 13° C.). This ribbon is utilized for encapsulation of medium chain tryiglyceride oil using 7.5 oval die. The capsules were dried and subjected for dissolution/disintegration analysis as per the requirement of current USP.

Example 26

Hydrophilic Enteric Soft Capsules Containing Bisacodyl

Acetic acid was added to polyethylene glycol (400) and mixed well. Bisacodyl was added to the polyethylene glycol/acetic acid mixture and mixed using a propeller mixture at 60° C. for 30 minutes (till completely dissolved).

| | |
|---|---|
| Bisacodyl | 1.40% |
| Acetic acid | 1.00% |
| Polyethylene glycol (400) | 97.60% |

Gel mass of Example 23 was cast into a ribbon with 0.03" thickness on a cold drum (10° C. to 13° C.). This ribbon was utilized for encapsulation of above-mentioned Bisacodyl fill using 7.5 oval die. The capsules were dried and subjected for dissolution/disintegration analysis as per the requirements of current USP.

Example 27

Hydrophobic Enteric Soft Capsules Containing Bisacodyl

Vegetable shortening, hydrogenated vegetable oil, and beeswax were melted with soybean oil at 65° C. To this wax mixture, Bisacodyl was added and mixed using a propeller mixer and the mix is cooled back to room temperature.

| | |
|---|---|
| Bisacodyl | 1.40% |
| Vegetable Shortening | 10.00% |
| Hydrogenated Soybean Oil | 2.50% |
| Beeswax | 2.50% |
| Soybean Oil | 83.60% |

Gel mass of Example 24 was cast into a ribbon with 0.03" thickness on a cold drum (10 to 13° C.). This ribbon was utilized for encapsulation of above-mentioned Bisacodyl fill using 7.5 oval die. The capsules were dried and subjected for dissolution/disintegration analysis as per the requirements of current USP.

Example 28

Methylene Blue Permeation Studies Using Dialysis Chamber

Methylene blue (water soluble dye) was dissolved in 0.1 N HCl placed on one side of the chamber and plain 0.1 N HCl on the other side of the chamber separated using enteric gel mass according to Example 1. This setup was placed in shaking water bath at 37° C., samples were removed up to 2 hours at periodic time intervals of 10, 20, 30, 45, 60, 90 and 120 minutes.

Up to 60 minutes, no significant release of methylene blue was observed. After 60 minutes, the release was less than 10%.

Example 29

Gel Masses Having Various Ratios of Gelatin-to-Polymer and Different Ribbon Thicknesses Gel masses made based on Example 24 where the enteric polymer and gelatin comprise 45% by weight were manufactured having polymer to gelatin weight ratios of 1:19 (5%), 1:9 (10%) and 1:5.7 (15%). The resulting gel masses were cast as films and characterized for enteric properties using USP disintegration and dissolution apparatus: 5, 10, and 15% polymer films failed the enteric disintegration test These experiments suggest that both 5 and 10% polymer concentration may not be enough to withstand the acidic pH (enteric properties) whereas 20% passes dissolution but really too weak for disintegration. Therefore 20% polymer may be minimum effective level of EUDRAGIT polymer to achieve acceptable enteric properties.

An 80:20 gelatin-to-polymer ratio gel mass was manufactured to verify the feasibility in the pilot gel reactor. The resulting gel mass was encapsulated at different ribbon thickness such as 0.015", 0.025" and 0.030" with two different speeds such as 3.0 and 3.5 RPM.

The 80:20 compositions with ammonium hydroxide, using EUDRAGIT formulations passed the enteric tests. After 3 months stability at 40° C./75% RH, the 80:20 composition were of border quality. The 70:30 ammonium hydroxide formulations with 0.035" 0.040", 0.045" and 0.050" ribbon thickness were attempted 0.035" ribbon thickness capsules, exhibited no swelling and stayed intact in SGF; they dissolved within 25 minutes in SIF. The 0.040" ribbon thickness capsules exhibited no swelling and stayed intact in SGF; they dissolved between 30 and 60 minutes in SIF. Thinner ribbons were also used for the same formula as shown in Table 1.

TABLE 1

Example Parameter and Testing Summary

| | Parameters | | | | USP Enteric Disintegration Test | |
|---|---|---|---|---|---|---|
| No. | Gelatin: Eudragit ® [A to B] | Eudragit ® solubilizer | Capsule size | Ribbon thickness | Acid | pH 6.8 |
| 1 | 70:30 | NH₄OH | 7.5 oval | 0.030" | Pass Intact capsules | Pass Disappeared in 30 minutes |
| 2 | 70:30 | NH₄OH | 7.5 oval | 0.025" | Pass Intact capsules | Pass Disappeared in 30 minutes |
| 3 | 70:30 | NH₄OH | 7.5 oval | 0.015" | Pass Intact capsules | Pass Disappeared in 15 minutes |

Example 30

Enteric Gel Mass Containing Cellulose Acetate Phthalate (CAP) and Using Ammonium Hydroxide as the Alkali Solubilizer A gel mass was made according to the formula below. The acid-insoluble polymer, (CAP) was dissolved in the water-alkali vehicle, and triethyl citrate was then added. The film-forming polymer, gelatin (lime bone, 150 bloom) was mixed with the plasticizer, glycerol, and added to the enteric polymer solution, mixed for 2 hours and kept overnight at 60° C.

| Cellulose Acetate Phthalate as 30% W/V dispersion | |
| --- | --- |
| CPD - 30 | 13.30% |
| Gelatin | 31.50% |
| Triethyl Citrate | 1.35% |
| Glycerol | 17.55% |
| Ammonium Hydroxide | 1.48% |
| Water | 34.82% |

Example 31

Enteric Gel Mass Containing Cellulose Acetate Phthalate (CAP) and Using Sodium Hydroxide as the Alkali Solubilizer A gel mass was made according to the formula below. The acid-insoluble polymer, CAP was dissolved in the water-alkali vehicle, and triethyl citrate was then added. The film-forming polymer, gelatin (lime bone, 150 bloom) was mixed with the plasticizer, glycerol, and added to the enteric polymer solution, mixed for 2 hours and kept overnight at 60° C.

| Cellulose Acetate Phthalate as 30% W/V dispersion | |
| --- | --- |
| CPD - 30 | 13.18% |
| Gelatin | 31.50% |
| Triethyl Citrate | 1.35% |
| Glycerol | 17.55% |
| Sodium Hydroxide | 1.60% |
| Water | 34.82% |

Example 32

Enteric Gel with Shellac

A gel mass was made according to the formula below. The acid-insoluble polymer shellac was dissolved in the water-alkali vehicle, and triethyl citrate was then added. The film-forming polymer, gelatin (lime bone, 150 bloom) was mixed with the plasticizer, glycerol, and added to the enteric polymer solution, mixed for 2 hours and kept overnight at 60° C.

| | |
| --- | --- |
| Ammoniated Shellac (25% W/V solution) | 36.00% |
| Gelatin | 36.00% |
| Glycerol | 18.00% |
| Triethyl citrate | 0.90% |
| Water | 9.10% |

Example 33

Preparation of Enteric Aspirin

Enteric aspirin tablets were made using the enteric gel mass of Example 24 and a rotary die machine as per the process described in U.S. Pat. Nos. 5,459,983, 5,146,730 and 6,482,516.

What is claimed is:

1. An enteric soft capsule shell formed from a gel mass composition comprising
   (a) a film-forming, water-soluble polymer,
   (b) an acid-insoluble polymer; and
   (c) an alkaline aqueous solvent;
      wherein the ratio of acid-insoluble polymer to film-forming, water soluble polymer is from 30:70 to 45:55 by weight;
      the final pH of the gel mass is less than or equal to about 9 pH units;
      and the moisture content of the enteric soft capsule shell formed from the gel mass composition is from about 2% to about 10%.

2. The enteric soft capsule shell of claim 1, wherein the film-forming, water-soluble polymer is proteinaceous.

3. The enteric soft capsule shell of claim 2, wherein the proteinaceous film-forming, water-soluble polymer is gelatin.

4. The enteric soft capsule shell of claim 3, wherein the gelatin is extracted from animal bones or skins, and has about 100 to about 250 blooms.

5. The enteric soft capsule shell of claim 1, wherein the film-forming, water-soluble polymer is a carbohydrate.

6. The enteric soft capsule shell of claim 5, wherein the carbohydrate is selected from the group consisting of hydroxypropyl methylcellulose and methyl cellulose.

7. The enteric soft capsule shell of claim 1, wherein the acid-insoluble polymer is selected from the group consisting of acrylic and methacrylic acid copolymers, cellulose acetate esters, hydroxypropyl methyl cellulose phthalate, and salts thereof.

8. The enteric soft capsule shell of claim 1, further comprising at least one plasticizer selected from the group consisting of sorbitol, glycerol, polyethylene glycol, poly-alcohols with 3 to 6 carbon atoms, citric acid, citric acid esters, triethyl citrate, and combinations thereof.

9. The enteric soft capsule shell of claim 1, wherein the alkaline aqueous solvent comprises an alkali selected from the group consisting of ammonia, sodium hydroxide, potassium hydroxide, ethylenediamine, hydroxylamine, and triethanolamine.

10. The enteric soft capsule shell of claim 1, wherein the alkaline aqueous solvent comprises a volatile alkali.

11. The enteric soft capsule shell of claim 10, wherein the volatile alkali is selected from the group consisting of ammonia and ethylenediamine.

12. The enteric soft capsule shell of claim 1, wherein the alkaline aqueous solvent is a hydroalcoholic solution.

13. The enteric soft capsule shell of claim 1, where the final pH of the gel mass is less than or equal to about 8.5.

14. The enteric soft capsule shell of claim 1, wherein the enteric soft capsule shell has a moisture content of from about 2% to about 10%.

15. The enteric soft capsule shell of claim 14, wherein the moisture content is from about 4% to about 8%.

16. The enteric soft capsule shell of claim 14, wherein the moisture content is about 8%.

17. The enteric soft capsule shell of claim 1, wherein the gel mass composition comprises a plasticizer, and the ratio of plasticizer to film-forming, water-soluble polymer is from about 1:9 to about 1:1 by weight.

18. The enteric soft capsule shell of claim 17, wherein the ratio of plasticizer to film-forming, water-soluble polymer is about 1:3 by weight.

\* \* \* \* \*